(12) United States Patent
Zhu et al.

(10) Patent No.: US 11,324,602 B2
(45) Date of Patent: May 10, 2022

(54) BIONIC ARTIFICIAL INTERPHALANGEAL JOINT

(71) Applicant: Hongwen Zhu, Tianjin (CN)

(72) Inventors: Hongwen Zhu, Tianjin (CN); Guofu Huang, Tianjin (CN); Ronghua Dong, Tianjin (CN); Tianmou Zhu, Tianjin (CN)

(73) Assignee: Hongwen Zhu, Tianjin (CN)

( * ) Notice: Subject to any disclaimer, the term of this patent is extended or adjusted under 35 U.S.C. 154(b) by 55 days.

(21) Appl. No.: 17/088,433

(22) Filed: Nov. 3, 2020

(65) Prior Publication Data

US 2021/0045889 A1 Feb. 18, 2021

(51) Int. Cl.
*A61F 2/42* (2006.01)
*A61F 2/30* (2006.01)

(52) U.S. Cl.
CPC .. *A61F 2/4241* (2013.01); *A61F 2002/30518* (2013.01); *A61F 2002/30528* (2013.01); *A61F 2002/30589* (2013.01); *A61F 2002/30594* (2013.01); *A61F 2002/30649* (2013.01); *A61F 2002/30662* (2013.01); *A61F 2002/4228* (2013.01); *A61F 2002/4243* (2013.01)

(58) Field of Classification Search
CPC ...... A61F 2002/4243; A61F 2002/4228; A61F 2/4241; A61F 2/4225; A61F 2002/4251; A61F 2002/4233; A61F 2002/30649; A61F 2002/30518; A61F 2002/30528; A61F 2002/3065; A61F 2002/30652; A61F 2002/30654; A61F 2002/30662; A61F 2002/30428
See application file for complete search history.

(56) References Cited

U.S. PATENT DOCUMENTS

| 4,106,128 A | * | 8/1978 | Greenwald | A61F 2/3804 623/21.13 |
| 4,304,011 A | * | 12/1981 | Whelan, III | A61F 2/4241 623/21.16 |
| 6,352,560 B1 | * | 3/2002 | Poeschmann | A61F 2/4241 623/21.16 |

(Continued)

FOREIGN PATENT DOCUMENTS

| DE | 3008292 A1 | * | 9/1980 | ........... A61F 2/4241 |
| FR | 3004921 B3 | * | 11/2015 | ........... A61F 2/4241 |

*Primary Examiner* — Javier G Blanco
(74) *Attorney, Agent, or Firm* — CBM Patent Consulting, LLC

(57) ABSTRACT

The present invention discloses a bionic artificial interphalangeal joint. The bionic artificial interphalangeal joint includes three sets of proximal prostheses and distal prostheses matched with the proximal prostheses and respectively corresponding to the three joints from the metacarpal bone to the distal phalanx. According to the specific position of the joint to be replaced, the corresponding artificial interphalangeal joint can be selected for replacement. Among them, the bionic artificial interphalangeal joint that can be installed between the metacarpal bone and the proximal phalanx has multiple degrees of freedom, which allows the proximal phalanx to bent in any direction like a real finger, and the bending angle of the proximal phalanx can be up to about 90 degrees when the proximal phalanx is bent toward the inner side of the finger.

8 Claims, 12 Drawing Sheets

(56) References Cited

U.S. PATENT DOCUMENTS

2010/0256770 A1\* 10/2010 Hakansson ........... A61F 2/4241
 623/21.16
2014/0188238 A1\* 7/2014 Sander .................. A61F 2/4241
 623/21.19

\* cited by examiner

BIONIC ARTIFICIAL INTERPHALANGEAL JOINT

This application claims priority to Chinese Patent Application Ser. No. CN2019110720073 filed on 5 Nov. 2019.

TECHNICAL FIELD

The invention relates to a medical artificial joint prosthesis, in particular an artificial interphalangeal joint.

BACKGROUND ART

Human hand bones include wrist bones, metacarpal bones and phalanges, and there are 14 phalanges, two sections in thumbs, and three sections in the NO. 2-5 fingers, which include proximal phalanx, middle phalanx and distal phalanx. The proximal end of the phalanx is the bottom, the middle is the body, and the distal end is the pulley. The distal phalanx has no pulley at the distal end, and its palm surface has a rough bulge, which is called the tuberosity of the distal phalanx, and the proximal phalanx is connected with the metacarpal bone.

Due to genetic degenerative diseases, arthritis and other diseases, the upper joint function of the patient's finger may be disordered, which may further cause local pain or even loss of joint function; in addition, joint dislocation or joint fracture and other injuries may also cause joint function disorder of the upper finger. With the further development of injuries, when the joint function is lost, a common treatment is to replace the joints between the fingers, using bionic artificial joints to replace the joints in the human body which have lost function, so that the fingers can restore basic functions.

Interdigital joint replacement surgery has been used in clinical practice for decades. During this process, artificial interdigital joints used to replace human interdigital joints have also undergone several updates. However, there are still many disadvantages for the interphalangeal joints in the prior art and need to be improved. For example, the existing artificial interphalangeal joints easily involve the muscles and tendons in the rotating structure, causing pain and discomfort; the connecting parts have insufficient degree of freedom, which makes it impossible for the fingers to make common movements after the operation, and thus have poor bionic performance; furthermore, due to insufficient degree of freedom, the muscle tissue of the human body will still exert a corresponding force on the artificial joint, thereby increasing the risk of artificial joint rupture; the requirements for the ligament muscle tissue are high, for many elderly patients, the artificial joint prosthesis cannot be replaced by operation, and there is a greater risk of dislocation.

In addition, there are 3 joints in the No. 2-5 fingers of the human body and two joints in the thumbs. The degree of freedom and strength of each joint is different. There is no specific bionic artificial prosthesis for different joints.

Due to the above-mentioned reasons, the inventors have conducted in-depth research on the existing artificial interphalangeal joints in order to design a new bionic artificial interphalangeal joint that can solve the above problems.

SUMMARY OF THE INVENTION

In order to overcome the above-mentioned problems, the inventor of the present invention has conducted intensive research and designed a bionic artificial interphalangeal joint. The bionic artificial interphalangeal joint includes three sets of proximal prostheses and corresponding distal prostheses; from the metacarpal to the distal phalanx, the corresponding artificial interphalangeal joint can be selected for replacement according to the specific position of the joint to be replaced. The bionic artificial interphalangeal joint that can be installed between the metacarpal and proximal phalanx has multiple degrees of freedom and can allow the proximal phalanx to bend in any direction like the real finger, and the bending angle of the proximal phalanx can be up to 90 degrees when it is bent to the inner side of the finger; it can be installed on the middle phalanx and the proximal phalanx. The bionic artificial interphalangeal joint between the phalanx makes the bending angle of the middle phalanx slightly greater than 90 degrees when it is bent to the inner side of the finger. It completely imitates the performance of the human finger during the bending process of each finger, and can guarantee the connection strength on each joint to prevent dislocation, thus completing the present invention.

Specifically, the object of the present invention is to provide a bionic artificial interphalangeal joint, which includes a proximal prosthesis 1 and a distal prosthesis 2 matched with the proximal prosthesis 1;

wherein the proximal end of the proximal prosthesis 1 is fixed on a metacarpal bone or a phalanx, and the distal end of the proximal prosthesis 1 is provided with a receiving groove 3, the distal end of the distal prosthesis 2 is fixed on the phalanx, and the proximal end of the distal prosthesis 2 is provided with a turning tip 4, a bowl-shaped gasket 5 is arranged between the receiving groove 3 and the turning tip 4, and the turning tip 4 is rotatably fixed on the bowl-shaped gasket 5, and the bowl-shaped gasket 5 is fixed in the receiving groove 3.

The bionic artificial interphalangeal joint includes:

a first proximal prosthesis 11 fixed proximally to a middle phalanx, and a first distal prosthesis 21 fixed distally to a distal phalanx, a first receiving groove 31 is opened on the distal end of the first proximal prosthesis 11, a first turning tip 41 is provided on the proximal end of the first distal prosthesis 21, a first bowl-shaped gasket 51 is provided between the first receiving groove 31 and the first turning tip 41, and the first turning tip 41 is fixed rotatably in the first bowl-shaped gasket 51, and the first bowl-shaped gasket 51 is fixed rotatably in the first receiving groove 31;

wherein, both the first turning tip 41 and the first bowl-shaped gasket 51 can only reciprocate in the same direction, when the first distal prosthesis 21 is bent toward the inner side of the finger relative to the first proximal prosthesis 11 under an action of external force, the first turning tip 41 and the first bowl-shaped gasket 51 firstly rotate relative to each other; and after the rotation reaches the limit position, the first bowl-shaped gasket 51 and the first receiving groove 31 can rotate relative to each other when the first distal prosthesis 21 receives a greater force.

The first distal prosthesis 21 is provided with a first bending limit stopper 61, when the first distal prosthesis 21 is bent at a predetermined angle relative to the first proximal prosthesis 11 under an action of external force, the first bending limit stopper 61 abuts against the first proximal prosthesis 11, thereby restricting the first distal prosthesis 21 from continuing to bend.

The bionic artificial interphalangeal joint further includes:

a second proximal prosthesis 12 fixed proximally to a proximal phalanx and a second distal prosthesis 22 fixed distally to a middle phalanx, a second receiving groove 32 is opened on the distal end of the second proximal prosthesis 12, a second turning tip 42 is provided on the proximal end of the second distal prosthesis 22, a second bowl-shaped gasket 52 is provided between the second receiving groove 32 and the second turning tip 42, and the second turning tip 42 is fixed rotatably in the second bowl-shaped gasket 52, and the second bowl-shaped gasket 52 is fixed rotatably in the second receiving groove 32;

wherein, both the second turning tip 42 and the second bowl-shaped gasket 52 can only reciprocate in the same direction;

when the second distal prosthesis 22 is bent toward the inner side of the finger relative to the second proximal prosthesis 12 under an action of external force, the second turning tip 42 and the second bowl-shaped gasket 52 firstly rotate relative to each other, and after the rotation reaches the limit position, the second bowl-shaped gasket 51 and the second receiving groove 32 can rotate relative to each other when the second distal prosthesis 22 receives a greater force.

The second distal prosthesis 22 is provided with a second bending limit stopper 62, when the second distal prosthesis 22 is bent at a predetermined angle relative to the second proximal prosthesis 12 under an action of external force, the second bending limit stopper 62 abuts against the second proximal prosthesis 12, thereby restricting the second distal prosthesis 22 from continuing to bend.

The proximal end of the second distal prosthesis 22 is provided with a second curved rod 72, and the second distal prosthesis 22 is connected with the second turning tip 42 through the second curved rod 72;

preferably, the second curved rod 72 is bent toward the inner side of the finger; more preferably, the second curved rod 72 is bent at an angle of 30 to 45 degrees.

The wall of the second receiving groove 32 is provided with a first notch 81 in the direction close to the inner side of the finger, The second bowl-shaped gasket 52 is provided with a second notch 82 in the direction close to the inner side of the finger, and when the second distal prosthesis 22 is bent, the second curved rod 72 can be inserted into the first notch 81 and the second notch 82, so that the bending angle of the second distal prosthesis 22 is above 90 degrees.

The bionic artificial interphalangeal joint further includes:

a third proximal prosthesis 13 fixed proximally to the metacarpal bone and a third distal prosthesis 23 fixed distally to the proximal phalanx, a third receiving groove 33 is opened on the distal end of the third proximal prosthesis 13, a third turning tip 43 is provided on the proximal end of the third distal prosthesis 23, a third bowl-shaped gasket 53 is provided between the third receiving groove 33 and the third turning tip 43, and the third turning tip 43 is fixed rotatably in the third bowl-shaped gasket 53, and the third bowl-shaped gasket 53 is fixed rotatably in the third receiving groove 33;

wherein, the third turning tip 43 can rotate in any direction, preferably, the proximal end of the third distal prosthesis 23 is provided with a third curved rod 73, and the third distal prosthesis 23 is connected with the third turning tip 43 through the third curved rod 73;

more preferably, the third curved rod 73 is bent toward the inner side of the finger;

the third curved rod 73 is bent at an angle of 30 to 45 degrees.

The wall of the third receiving groove 33 is provided with a third notch 83 in the direction close to the inner side of the finger, the third bowl-shaped gasket 53 is provided with a fourth notch 84 in the direction close to the inner side of the finger, and when the third distal prosthesis 23 is bent to the inner side of the finger, the third curved rod 73 can be inserted into the third notch 83 and the fourth notch 84, so that the third distal prosthesis 23 is bent toward the inner side of the finger at an angle above 90 degrees.

The third distal prosthesis 23 is provided with a third bending limit stopper 63, when the third distal prosthesis 23 is bent at a predetermined angle relative to the third proximal prosthesis 13 under an action of external force, the third bending limit stopper 63 abuts against the third proximal prosthesis 13, thereby restricting the third distal prosthesis 23 from continuing to bend.

The beneficial effects of the present invention include:

(1) the bionic artificial interphalangeal joint provided according to the present invention includes multiple joint structures, and the corresponding artificial interphalangeal joint can be selected for replacement according to different joint positions, which greatly improves the adaptability of the bionic artificial interphalangeal joint;

(2) the bionic artificial interphalangeal joint provided by the present invention is provided with a bowl-shaped gasket, which not only reduces the wear rate, but also improves the flexibility and adaptability of the fingers after surgery; and (3) the bowl-mounted gasket can reduce impact and avoid static electricity.

DESCRIPTION OF THE REFERENCE SIGNS

Figure 1:
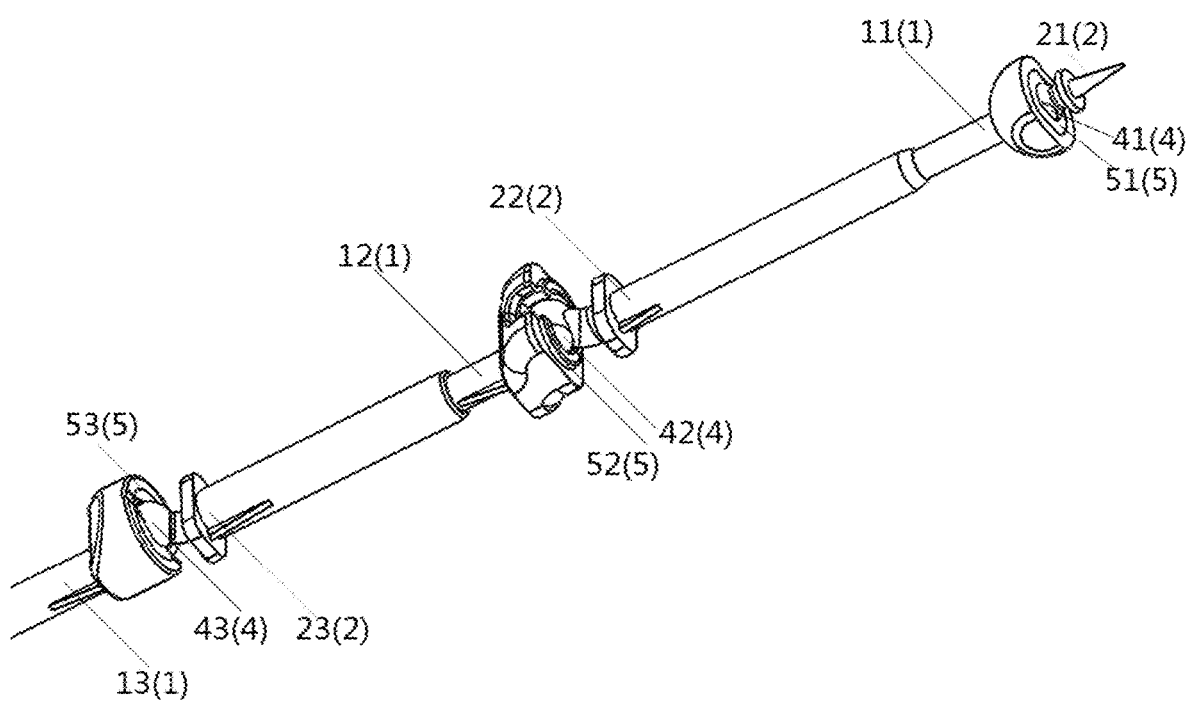
FIG. 1 shows a schematic diagram of the overall structure of a bionic artificial interphalangeal joint according to a preferred embodiment of the present invention.

1—proximal prosthesis
11—first proximal prosthesis
12—second proximal prosthesis
13—third proximal prosthesis
2—distal prosthesis
21—first distal prosthesis
22—second distal prosthesis
23—third distal prosthesis
3—receiving groove
31—first receiving groove
32—second receiving groove
33—third receiving groove
4—turning tip
41—first turning tip
42—second turning tip
43—third turning tip
5—bowl gasket
51—first bowl-shaped gasket
52—second bowl-shaped gasket
53—third bowl-shaped gasket
61—first bending limit stopper
62—second bending limit stopper
63—third bending limit stopper
72—second curved rod
73—third curved rod
81—first notch
82—second notch
83—third notch
84—fourth notch

SPECIFIC EMBODIMENTS FOR CARRYING OUT THE INVENTION

Hereinafter, the present invention will be explained in more detail with reference to figures and examples. Through these explanations, the features and advantages of the present invention will become clearer.

The term "exemplary" as used herein is intended to be "serving as an example, an embodiment, or an illustrative embodiment." Any of the embodiments described herein as "exemplary" need not be construed as preferred as or better than other embodiments. Although various aspects of the embodiments are shown in the figures, it is not necessary to draw a figure in proportion unless otherwise specified.

In the present application, the distal end refers to the end close to the tip of the finger, and the proximal end refers to the end close to the arm.

The proximal prosthesis and the distal prosthesis described in the present application are a pair of prostheses that work in cooperation with each other. They are respectively fixed on the bones of two adjacent fingers, and the contact part is the interphalangeal joint.

According to a bionic artificial interphalangeal joint provided by the present invention, as shown in FIGS. 1, 5, 9, and 10, the bionic artificial interphalangeal joint includes a proximal prosthesis 1 and a distal prosthesis 2 matched with the proximal prosthesis 1; the contact part between the adjacent proximal prosthesis 1 and the distal prosthesis 2 is the joint;

wherein the proximal end of the proximal prosthesis 1 is fixed on a metacarpal bone or a phalanx, and the distal end of the proximal prosthesis 1 is provided with a receiving groove 3, the distal end of the distal prosthesis 2 is fixed on the phalanx, and the proximal end of the distal prosthesis 2 is provided with a turning tip 4, preferably, there are many methods to fix the proximal prosthesis, the distal prosthesis and the metacarpal bone or the phalanx; in the present application, the method of insertion and fixation is preferably selected, namely, the proximal end of the proximal prosthesis and the distal end of the distal prosthesis are set in the shape of a thin rod, which is inserted into the metacarpal or phalanx where the phalanx, phalanx base and other parts are removed and fixed by means of bone cement or biomaterial spraying; structures such as threads can also be carved on the thin rod to increase friction and improve stability; the phalanges described in the present application include proximal phalanx, middle phalanx and distal phalanx.

A bowl-shaped gasket 5 is arranged between the receiving groove 3 and the turning tip 4, and the turning tip 4 is rotatably fixed on the bowl-shaped gasket 5, and the bowl-shaped gasket 5 is fixed in the receiving groove 3. The bowl-shaped gasket 5 and the receiving groove 3 can be optionally set to be relatively rotatable or non-rotatable.

The size and shape of the inside of the receiving groove 3 are basically the same as the size and shape of the outer surface of the bowl-shaped gasket 5, and the size and shape of the inside of the bowl-shaped gasket 5 are basically the same as the size and shape of the outer surface of the turning tip 4; preferably, the wall thickness of the bowl-shaped gasket 5 is the same at any location.

In a preferred embodiment, as shown in FIGS. 1, 2, 3, 4, and 5, the bionic artificial interphalangeal joint includes:

a first proximal prosthesis 11 fixed proximally to a middle phalanx, and a first distal prosthesis 21 fixed distally to a distal phalanx, a first receiving groove 31 is opened on the distal end of the first proximal prosthesis 11, a first turning tip 41 is provided on the proximal end of the first distal prosthesis 21, a first bowl-shaped gasket 51 is provided between the first receiving groove 31 and the first turning tip 41, and the first turning tip 41 is fixed rotatably in the first bowl-shaped gasket 51, and the first bowl-shaped gasket 51 is fixed rotatably in the first receiving groove 31;

wherein, both the first turning tip 41 and the first bowl-shaped gasket 51 can only reciprocate in the same direction, when the first distal prosthesis 21 is bent toward the inner side of the finger relative to the first proximal prosthesis 11 under an action of external force, the first turning tip 41 and the first bowl-shaped gasket 51 firstly rotate relative to each other; and after the rotation reaches the limit position, the first bowl-shaped gasket 51 and the first receiving groove 31 can rotate relative to each other when the first distal prosthesis 21 receives a greater force. Preferably, when the rotation reaches the limit position, the rotation angle is 70 to 80 degrees.

A rotation limit structure is provided on the first bowl-shaped gasket 51 and the first turning tip 41, which can allow the two to rotate relative to a certain angle, such as about 10 degrees, and which will be locked by mechanical limit after reaching the maximum allowable angle.

The tightness between the first turning tip 41 and the first bowl-shaped gasket 51 is less than the tightness between the first bowl-shaped gasket 51 and the first receiving groove 31.

Figure 2:
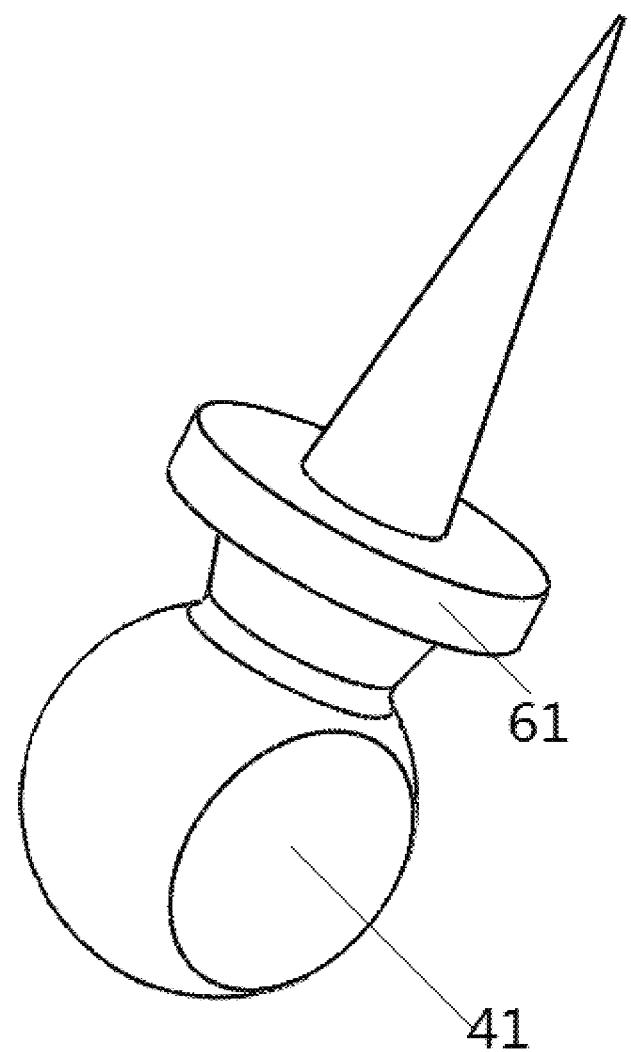
FIG. 2 shows a schematic structural diagram of a first distal prosthesis in a bionic artificial interphalangeal joint according to a preferred embodiment of the present invention.
Figure 3:
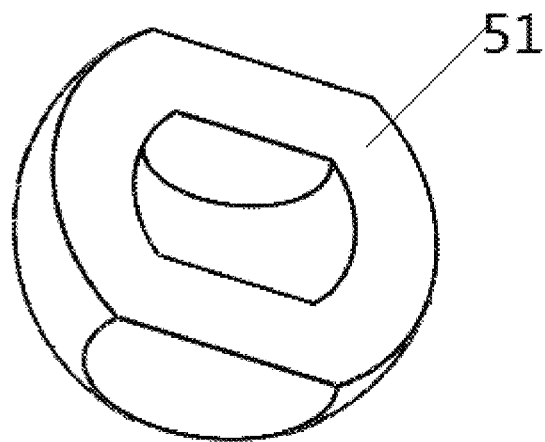
FIG. 3 shows a schematic structural diagram of a first bowl-shaped gasket in a bionic artificial interphalangeal joint according to a preferred embodiment of the present invention.
Figure 4:
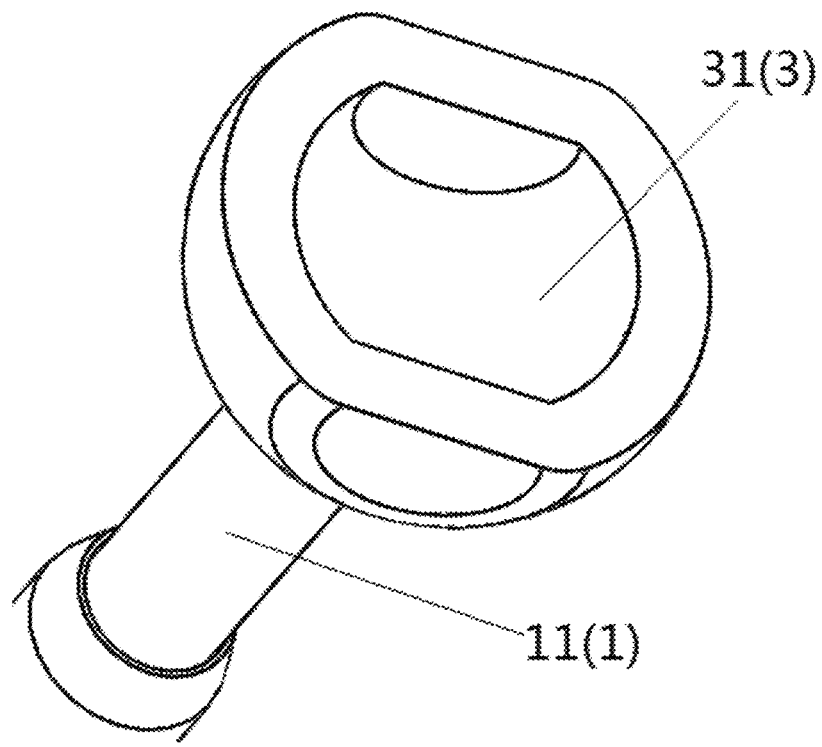
FIG. 4 shows a schematic structural diagram of the first proximal prosthesis in the bionic artificial interphalangeal joint according to a preferred embodiment of the present invention.

Preferably, the first turning tip 41 is similar to a drum shape as shown in FIG. 2; specifically, on the basis of a spherical shape, the two ends of the spherical shape are symmetrically cut to obtain two planes which are parallel to each other, thus obtaining the shape of the first turning tip 41 of the present application.

The size and shape of the inside of the first receiving groove 31 are basically the same as the size and shape of the outer surface of the first bowl-shaped gasket 51, and the size and shape of the inside of the first bowl-shaped gasket 51 are the basically same as the size and shape of the first turning tip 41.

Figure 5:
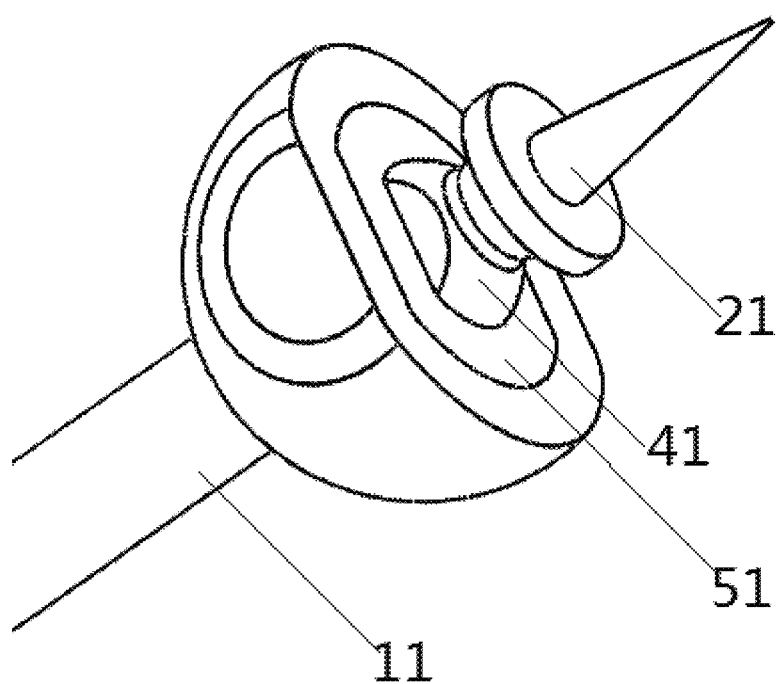
FIG. 5 shows a partial enlarged view of the connection between the first proximal prosthesis and the first distal prosthesis in the bionic artificial interphalangeal joint according to a preferred embodiment of the present invention.

In a preferred embodiment, as shown in FIGS. 1, 2 and 5, the first distal prosthesis 21 is provided with a first bending limit stopper 61, when the first distal prosthesis 21 is bent at a predetermined angle relative to the first proximal prosthesis 11 under an action of external force, the first bending limit stopper 61 abuts against the first proximal prosthesis 11, thereby restricting the first distal prosthesis 21 from continuing to bend. Preferably, the predetermined angle is 80 to 90 degrees.

In a preferred embodiment, as shown in FIGS. 1, 6, 7, 8, and 9, the bionic artificial interphalangeal joint includes:

a second proximal prosthesis 12 fixed proximally to a proximal phalanx and a second distal prosthesis 22 fixed distally to a middle phalanx, a second receiving groove 32 is opened on the distal end of the second proximal prosthesis 12, a second turning tip 42 is provided on the proximal end of the second distal prosthesis 22, a second bowl-shaped gasket 52 is provided between the second receiving groove 32 and the second turning tip 42, and the second turning tip 42 is fixed rotatably in the second bowl-shaped gasket 52, and the second bowl-shaped gasket 52 is fixed rotatably in the second receiving groove 32;

wherein, both the second turning tip 42 and the second bowl-shaped gasket 52 can only reciprocate in the same direction;

when the second distal prosthesis 22 is bent toward the inner side of the finger relative to the second proximal prosthesis 12 under an action of external force, the second turning tip 42 and the second bowl-shaped gasket 52 firstly rotate relative to each other, and after the rotation reaches the limit position, the second bowl-shaped gasket 51 and the second receiving groove 32 can rotate relative to each other when the second distal prosthesis 22 receives a greater force. Preferably, when the rotation reaches the limit position, the rotation angle is 80 to 90 degrees.

The tightness between the second turning tip 42 and the second bowl-shaped gasket 52 is less than the tightness between the second bowl-shaped gasket 52 and the second receiving groove 32.

A rotation limit structure is provided on the second bowl-shaped gasket 52 and the second turning tip 42, which can allow the two to rotate relative to a certain angle, such as about 10 degrees, and which will be locked by mechanical limit after reaching the maximum allowable angle.

Figure 6:
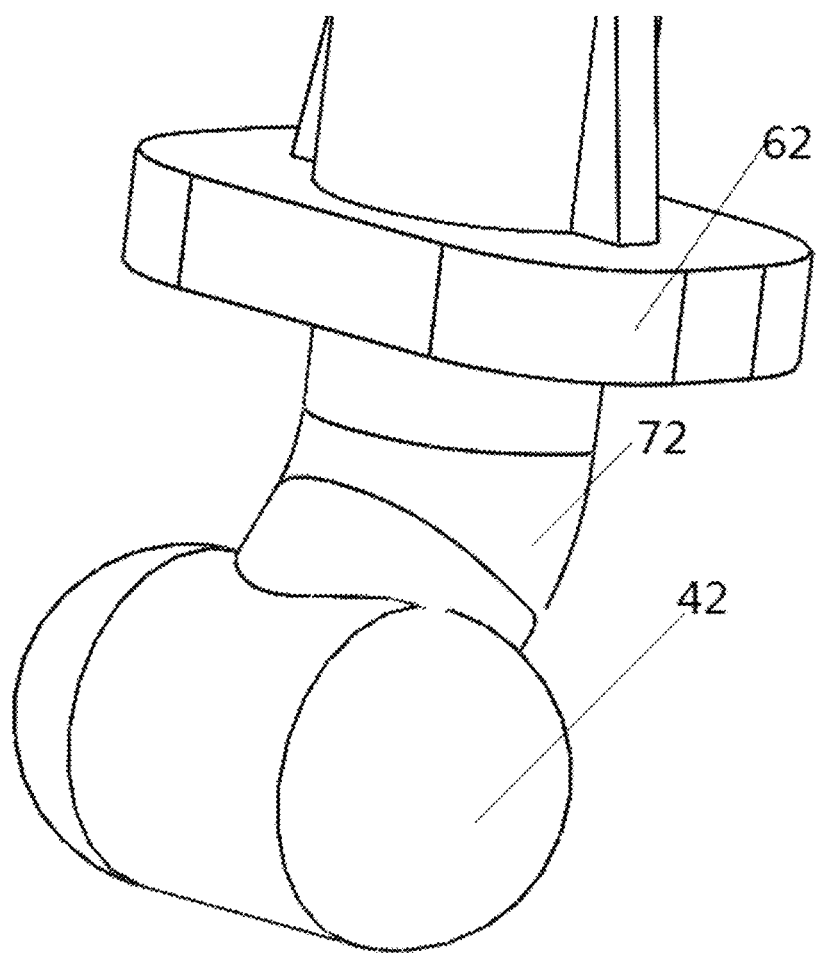
FIG. 6 shows a schematic structural diagram of a second distal prosthesis in a bionic artificial interphalangeal joint according to a preferred embodiment of the present invention.
Figure 7:
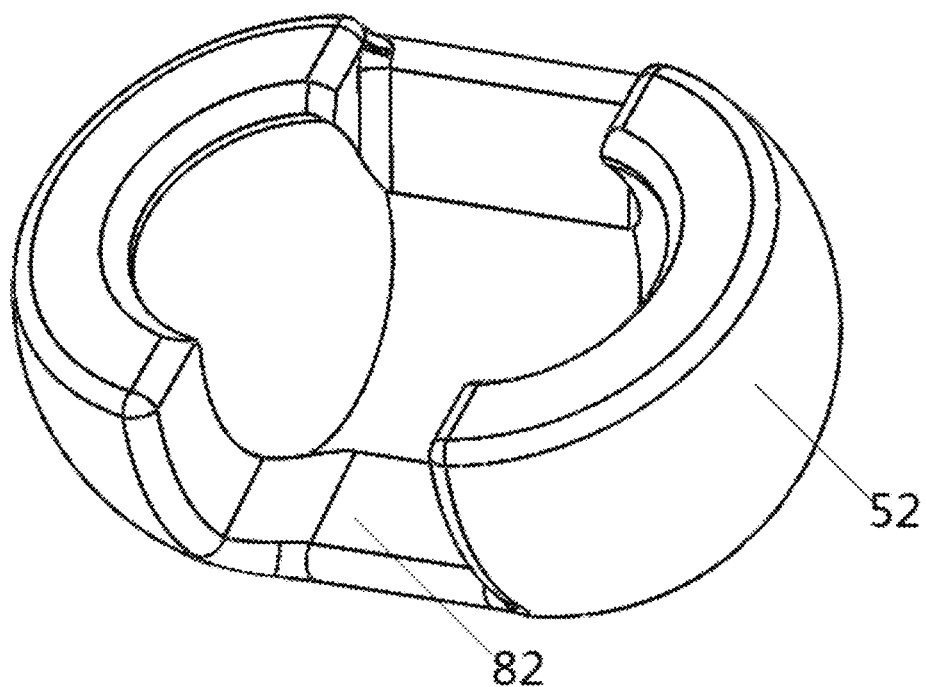
FIG. 7 shows a schematic structural view of a second bowl-shaped gasket in a bionic artificial interphalangeal joint according to a preferred embodiment of the present invention.
Figure 8:
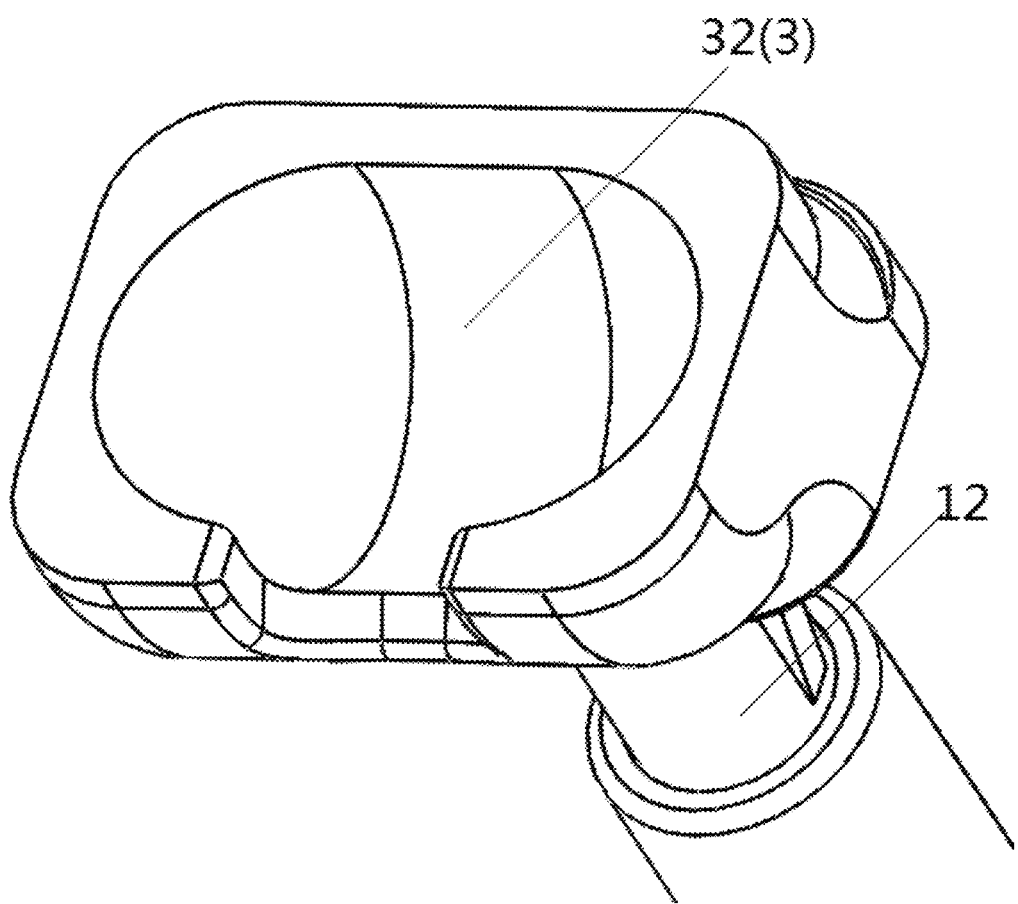
FIG. 8 shows a schematic structural diagram of a second proximal prosthesis in a bionic artificial interphalangeal joint according to a preferred embodiment of the present invention.

Preferably, the second turning tip 42 is similar to the shape of a round rod as shown in FIG. 6; specifically, the second turning tip 42 includes a round rod located in the middle, and is located at both ends of the round rod. A hemispherical end is provided, and the radius of the hemispherical is consistent with the radius of the round rod; therefore, the second turning tip 42 can only reciprocate in one direction inside the second bowl-shaped gasket 52.

In addition, by setting the second turning tip 42 as a round rod shape, the stability of the second turning tip 42 can be improved to prevent the second turning tip 42 from lateral rotation/deflection, so that the second distal prosthesis 22 connected to the second turning tip can only bend toward the inner side of the finger.

In a preferred embodiment, the second distal prosthesis 22 is provided with a second bending limit stopper 62, when the second distal prosthesis 22 is bent at a predetermined angle relative to the second proximal prosthesis 12 under an action of external force, the second bending limit stopper 62 abuts against the second proximal prosthesis 12, thereby restricting the second distal prosthesis 22 from continuing to bend. Preferably, the predetermined angle is 100 to 110 degrees.

In a preferred embodiment, the proximal end of the second distal prosthesis 22 is provided with a second curved rod 72, and the second distal prosthesis 22 is connected with the second turning tip 42 through the second curved rod 72; preferably, the second curved rod 72 is bent toward the inner side of the finger/hand center;

more preferably, the second curved rod 72 is bent at an angle of 30 to 45 degrees; the length of the second curved rod 72 is relatively small, and the setting of the second curved rod 72 can further improve the bionic performance of the artificial interphalangeal joint in the present application, increase the connection strength of the bionic artificial interphalangeal joint, and reduce the risk of dislocation.

Figure 9:
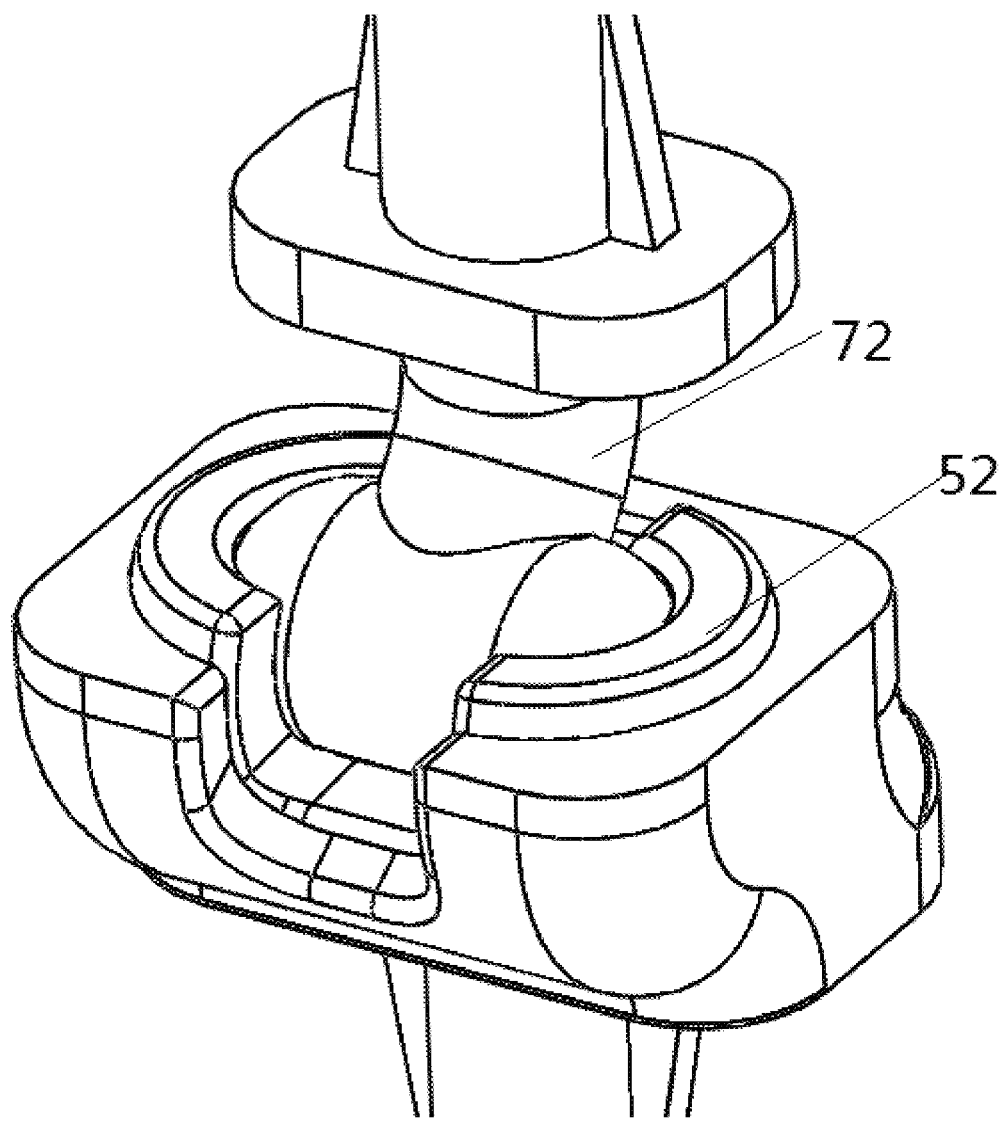
FIG. 9 shows a partial enlarged view of the connection between the second proximal prosthesis and the second distal prosthesis in the bionic artificial interphalangeal joint according to a preferred embodiment of the present invention.

Specifically, the joint between the middle phalanx and the proximal phalanx is much stressed. In order to ensure its connection strength, the second bowl-shaped gasket 52 needs to be made greater to cover a greater area of the second turning tip 42. As shown in FIG. 9, 60% to 70% of the second turning tip 42 is covered by the second bowl-shaped gasket 52, making it difficult to dislocate between the two. In the case of a large coverage, the maximum relative rotation between the two is limited. If a straight rod is used instead of the curved rod 72, the maximum rotation angle of the second turning tip 42 in the second bowl-shaped gasket 52 will be greatly limited, and the maximum rotation angle in a single direction is only about 50 degrees; and after the second turning tip 42 is connected through the second curved rod 72, the second curved rod 72 is matched with the notch, and the maximum rotation angle of the turning tip 42 in the second bowl-shaped gasket 52 can reach above 90 degrees.

In a preferred embodiment, the wall of the second receiving groove 32 is provided with a notch 81 in the direction close to the inner side of the finger, The wall of the second receiving groove 32 is provided with a first notch 81 in the direction close to the inner side of the finger, the second bowl-shaped gasket 52 is provided with a second notch 82 in the direction close to the inner side of the finger, and when the second distal prosthesis 22 is bent, the second curved rod 72 can be inserted into the first notch 81 and the second notch 82, so that the bending angle of the second distal prosthesis 22 is above 90 degrees.

More preferably, the second bowl-shaped gasket 52 is provided with a notch in the direction opposite to the second notch 82. The purpose of the notch is to place the curved rod 72 so that when the fingers are in a straightened state, the second curved rod 72 will not interfere with the second bowl-shaped gasket 52.

In a preferred embodiment, as shown in FIGS. 10, 11, 12 and 13, the bionic artificial interphalangeal joint further includes:

a third proximal prosthesis 13 fixed proximally to the metacarpal bone and a third distal prosthesis 23 fixed distally to the proximal phalanx, a third receiving groove 33 is opened on the distal end of the third proximal prosthesis 13, a third turning tip 43 is provided on the proximal end of the third distal prosthesis 23, a third bowl-shaped gasket 53 is provided between the third receiving groove 33 and the third turning tip 43, and the third turning tip 43 is fixed rotatably in the third bowl-shaped gasket 53, and the third bowl-shaped gasket 53 is fixed rotatably in the third receiving groove 33;

wherein, the third turning tip 43 can rotate in any direction, preferably, the proximal end of the third distal prosthesis 23 is provided with a third curved rod 73, and the third distal prosthesis 23 is connected with the third turning tip 43 through the third curved rod 73;

more preferably, the third curved rod 73 is bent toward the inner side of the finger;

the third curved rod 73 is bent at an angle of 30 to 45 degrees. The length of the third curved rod 73 is relatively small, and the setting of the third curved rod 73 can further enhance the bionic performance of the artificial interphalangeal joint in the present application, improve the connection strength of the bionic artificial interphalangeal joint, and reduce the risk of dislocation.

Figure 10:
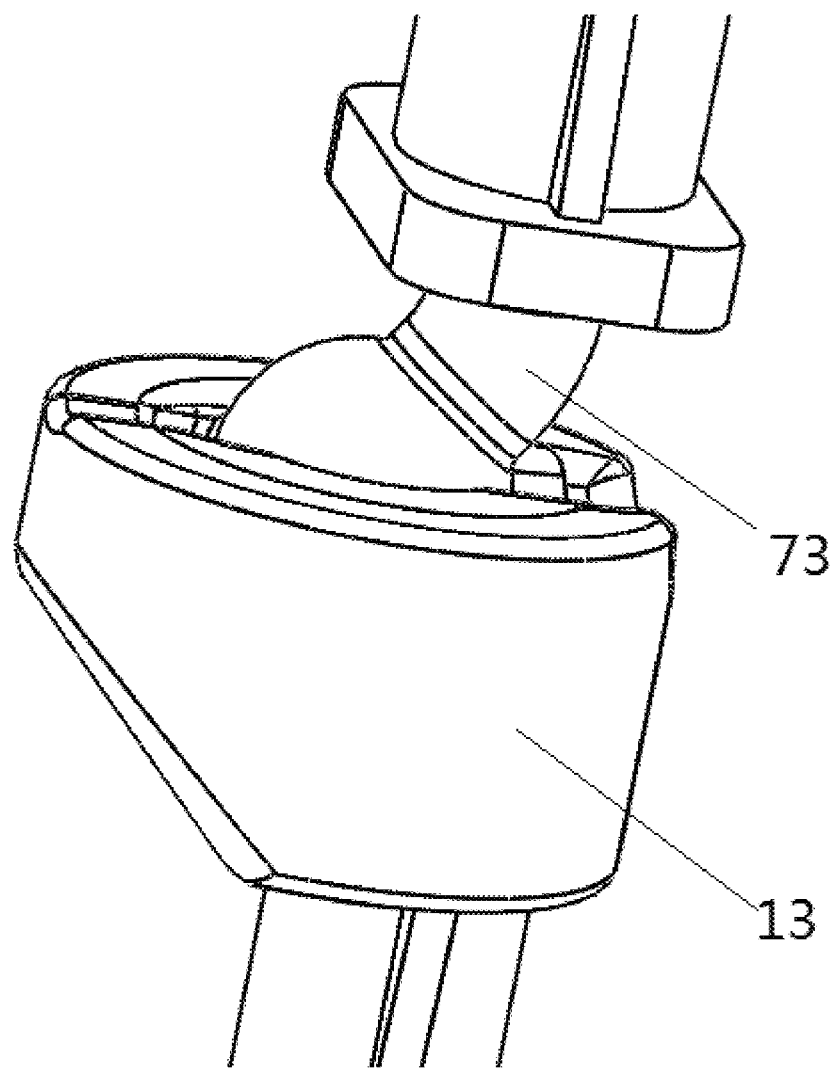
FIG. 10 shows a partial enlarged view of the connection between the third proximal prosthesis and the third distal prosthesis in the bionic artificial interphalangeal joint according to a preferred embodiment of the present invention.
Figure 11:
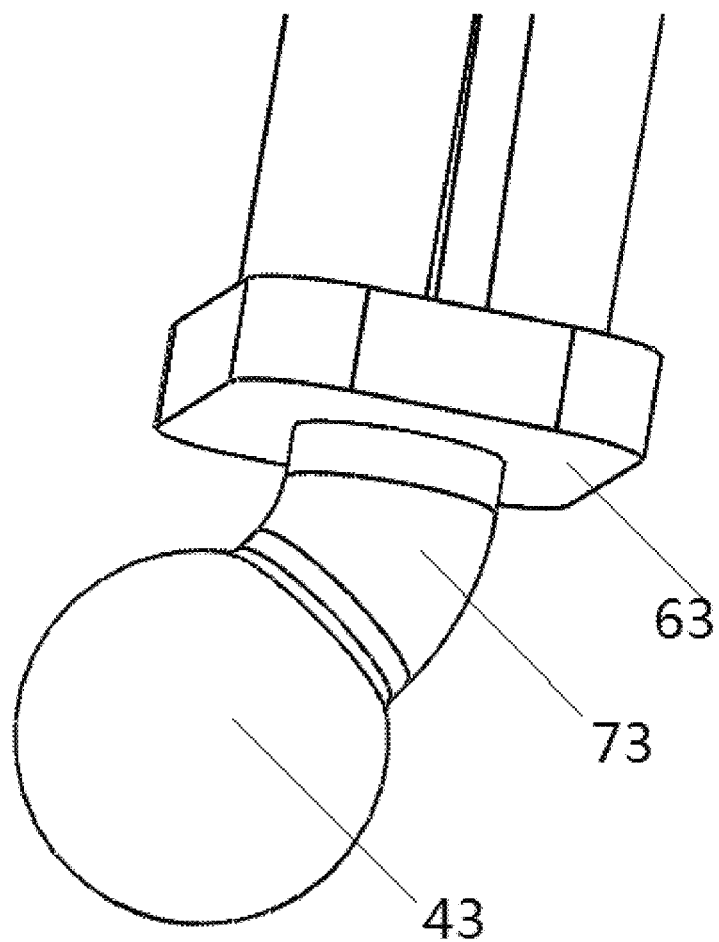
FIG. 11 shows a schematic structural diagram of a third distal prosthesis in a bionic artificial interphalangeal joint according to a preferred embodiment of the present invention.
Figure 12:
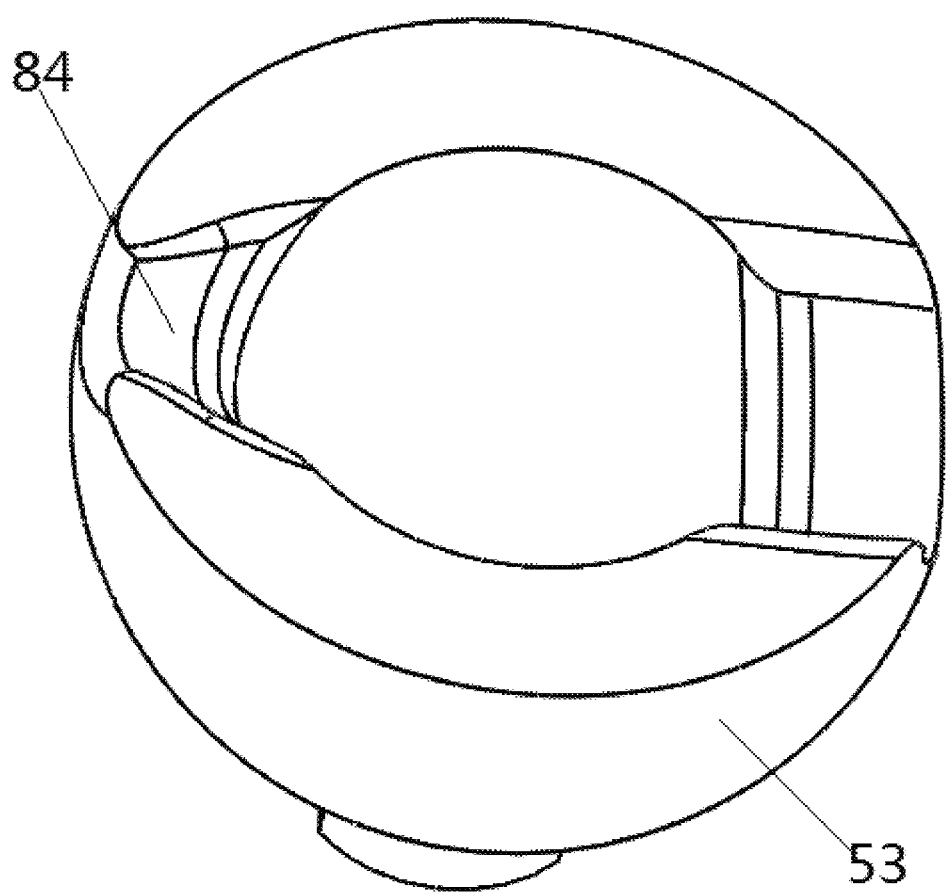
FIG. 12 shows a schematic structural view of a third bowl-shaped gasket in a bionic artificial interphalangeal joint according to a preferred embodiment of the present invention.
Figure 13:
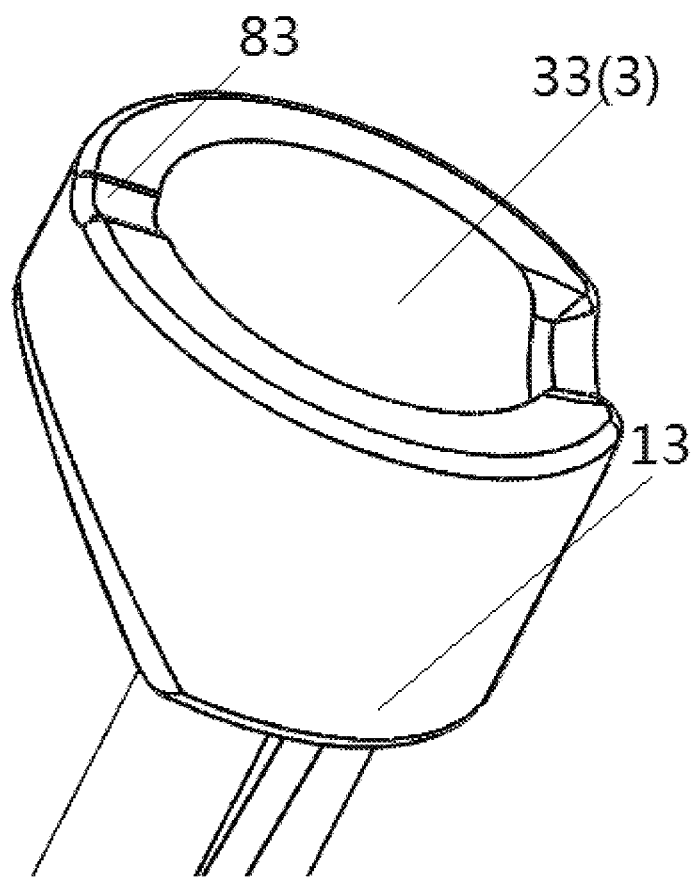
FIG. 13 shows a schematic structural diagram of a third proximal prosthesis in a bionic artificial interphalangeal joint according to a preferred embodiment of the present invention.

Specifically, the joint between the metacarpal bone and the proximal phalanx is much stressed. In order to ensure its connection strength, the third bowl-shaped gasket 53 needs to be made greater to cover a greater area of the third turning tip 43. As shown in FIG. 10, 50% to 60% of the third turning tip 43 is covered by the third bowl-shaped gasket 53, making it difficult to dislocate between the two. In the case of a large coverage, the maximum relative rotation between the two is limited. If a straight rod is used instead of the third curved rod 73, the maximum rotation angle of the third turning tip 43 in the third bowl-shaped gasket 53 will be greatly restricted, and can only rotate about 50 degrees in a single direction; and after the third turning tip 43 is connected through the third curved rod 73, the third turning tip is matched with the notch through the third curved rod 73, and the maximum rotation angle of the third turning tip 43 in the third bowl-shaped gasket 53 can reach about 90 degrees.

In a preferred embodiment, the wall of the third receiving groove 33 is provided with a third notch 83 in the direction close to the inner side of the finger.

The third bowl-shaped gasket 53 is provided with a fourth notch 84 in the direction close to the inner side of the finger. The widths of the third notch 83 and the fourth notch 84 are slightly greater than the diameter of the curved rod 73.

When the third distal prosthesis 23 is bent to the inner side of the finger, the third curved rod 73 can be inserted into the third notch 83 and the fourth notch 84, so that the third distal prosthesis 23 is bent toward the inner side of the finger at an angle above 90 degrees.

When the third distal prosthesis 23 is bent in other directions except the inner side of the finger, the curved rod 73 can only rotate about 50 degrees under the obstruction of the third bowl-shaped gasket 53, which is basically the same as the function of normal human fingers.

In a preferred embodiment, the third receiving groove 33 and the third bowl-shaped gasket 53 cannot rotate relative to each other, and a downwardly protruding boss is provided at the bottom of the third bowl-shaped gasket 53. The bottom of the third receiving groove 33 is provided with a notch, which is basically the same in terms of size and shape as the boss, and can just accommodate the boss; preferably, the boss has an edge, such as a cube or a hexagonal prism. Therefore, after the third bowl-shaped gasket 53 is placed in the third receiving groove 33, the third bowl-shaped gasket 53 and the third receiving groove 33 cannot rotate/roll relative to each other.

In a preferred embodiment, the third distal prosthesis 23 is provided with a third bending limit stopper 63, when the third distal prosthesis 23 is bent at a predetermined angle relative to the third proximal prosthesis 13 under an action of external force, the third bending limit stopper 63 abuts against the third proximal prosthesis 13, thereby restricting the third distal prosthesis 23 from continuing to bend. In actual use, the third bending limit stopper 63 is mainly used to limit the third distal prosthesis 23 when the third distal prosthesis 23 is bent to the inner side of the finger. When the third distal prosthesis 23 is bent in other directions, the third bowl-shaped gasket 53 itself can play a specific limiting role.

As shown in FIG. 1, the bionic artificial interphalangeal joint provided by the present application includes three proximal prostheses and three distal prostheses, which constitute three sets of joints, respectively being: a bionic joint composed of a first proximal prosthesis 11 and a first distal prosthesis 21 used between the middle phalanx and the distal phalanx; a bionic joint composed of a second proximal prosthesis 12 and a second distal prosthesis 22 used between the proximal phalanx and the distal phalanx; and a bionic joint composed of a third proximal prosthesis 31 and a third distal prosthesis 33 used between the metacarpal bone and the proximal phalanx. In actual use, any one or more of these groups can be selected. Because each group corresponds to a specific finger position, its adaptability is greater and the postoperative recovery effect is more ideal.

In the description of the present invention, it should be noted that the terms "upper," "lower," "inner," "outer," "front," "rear" and other directions or positional relationships are based on the working state of the present invention, only for the convenience of describing the invention and simplifying the description, rather than indicating or implying that the device or element pointed out must have a specific orientation, be constructed and operated in a specific orientation. Therefore, these terms cannot be understood as limiting the present invention. In addition, the terms "first", "second" and "third" are only used for descriptive purposes, and cannot be understood as indicating or implying relative importance.

The above describes the present invention in combination with preferred embodiments, but these embodiments are only exemplary and merely serve for illustration. On this basis, various replacements and improvements can be made to the present invention, all of which fall within the protection scope of the present invention.

What is claimed is:

1. A bionic artificial interphalangeal joint comprising:
a first middle phalanx prosthesis (11) sized and configured to be fixed proximally to a middle phalanx, and a first distal phalanx prosthesis (21) sized and configured to be fixed distally to a distal phalanx, the first middle phalanx prosthesis (11) sized and configured to articulate with the first distal phalanx prosthesis (21), wherein:
a proximal end of the first middle phalanx prosthesis (11) is sized and configured to be fixed to a middle phalanx, and a distal end of the first middle phalanx prosthesis (11) is provided with a first receiving groove (31),
a distal end of the first distal phalanx prosthesis (21) is sized and configured to be fixed to a distal phalanx, and a proximal end of the first distal phalanx prosthesis (21) is provided with a first turning tip (41),
a first bowl-shaped gasket (51) is provided between the first receiving groove (31) and the first turning tip (41), and the first turning tip (41) is fixed rotatably in the first bowl-shaped gasket (51), and the first bowl-shaped gasket (51) is fixed rotatably in the first receiving groove (31);
wherein, both the first turning tip (41) and the first bowl-shaped gasket (51) can only reciprocate in the same direction, when the first distal phalanx prosthesis (21) is bent toward the inner side of the finger relative to the first middle phalanx prosthesis (11) under an action of external force, the first turning tip (41) and the first bowl-shaped gasket (51) firstly rotate relative to each other; and after the rotation reaches the limit position, the first bowl-shaped gasket (51) and the first receiving groove (31) can rotate relative to each other when the first distal phalanx prosthesis (21) receives a greater force, and
a second proximal phalanx prosthesis (12) sized and configured to be fixed proximally to a proximal phalanx, and a second middle phalanx prosthesis (22) sized and configured to be fixed distally to the middle phalanx, the second proximal phalanx prosthesis (12) sized and configured to articulate with the second middle phalanx prosthesis (22), wherein:
a proximal end of the second proximal phalanx prosthesis (12) is sized and configured to be fixed to a proximal phalanx, and a distal end of the second proximal phalanx prosthesis (12) is provided with a second receiving groove (32),
a distal end of the second middle phalanx prosthesis (22) is sized and configured to be fixed to a middle phalanx, and a proximal end of the second middle phalanx prosthesis (22) is provided with a second turning tip (42),
a second bowl-shaped gasket (52) is provided between the second receiving groove (32) and the second turning tip (42), and the second turning tip (42) is fixed rotatably in the second bowl-shaped gasket (52), and the second bowl-shaped gasket (52) is fixed rotatably in the second receiving groove (32);
wherein, both the second turning tip (42) and the second bowl-shaped gasket (52) can only reciprocate in the same direction, when the second middle phalanx prosthesis (22) is bent toward the inner side of the finger relative to the second proximal phalanx prosthesis (12) under an action of external force, the second turning tip (42) and the second bowl-shaped gasket (52) firstly rotate relative to each other; and after the rotation reaches the limit position, the second bowl-shaped gasket (52) and the second receiving groove (32) can rotate relative to each other when the second middle phalanx prosthesis (22) receives a greater force,
wherein the size and shape of the first turning tip (41) is different from the size and shape of the second turning tip (42).

2. The bionic artificial interphalangeal joint according to claim 1, characterized in that:
the first distal phalanx prosthesis (21) is provided with a first bending limit stopper (61), when the first distal phalanx prosthesis (21) is bent at a predetermined angle relative to the first middle phalanx prosthesis (11) under an action of external force, the first bending limit stopper (61) abuts against the first middle phalanx prosthesis (11), thereby restricting the first distal phalanx prosthesis (21) from continuing to bend.

3. The bionic artificial interphalangeal joint according to claim 1, wherein:
the second middle phalanx prosthesis (22) is provided with a second bending limit stopper (62), when the second middle phalanx prosthesis (22) is bent at a predetermined angle relative to the second proximal phalanx prosthesis (12) under an action of external force, the second bending limit stopper (62) abuts against the second proximal phalanx prosthesis (12), thereby restricting the second middle phalanx prosthesis (22) from continuing to bend.

4. The bionic artificial interphalangeal joint according to claim 1, wherein:
the proximal end of the second middle phalanx prosthesis (22) is provided with a second curved rod (72), and the second middle phalanx prosthesis (22) is connected with the second turning tip (42) through the second curved rod (72);
the second curved rod (72) is sized and configured to be bent toward the inner side of the finger;
the second curved rod (72) is sized and configured to be bent at an angle of 30 to 45 degrees.

5. The bionic artificial interphalangeal joint according to claim 4, characterized in that:
a wall of the second receiving groove (32) is provided with a first notch (81) in the direction close to the inner side of the finger,
the second bowl-shaped gasket (52) is provided with a second notch (82) in the direction close to the inner side of the finger,
and when the second middle phalanx prosthesis (22) is bent, the second curved rod (72) can be inserted into the first notch (81) and the second notch (82), so that the bending angle of the second middle phalanx prosthesis (22) is above 90 degrees.

6. The bionic artificial interphalangeal joint according to claim 1, wherein:
the bionic artificial interphalangeal joint further includes:
a third metacarpal prosthesis (13) sized and configured to be fixed proximally to a metacarpal bone and a third proximal phalanx prosthesis (23) sized and configured to be fixed distally to the proximal phalanx, wherein:
a proximal end of the third metacarpal prosthesis (13) is sized and configured to be fixed to the metacarpal bone, and a distal end of the third metacarpal prosthesis (13) is provided with a third receiving groove (33), a distal end of the third proximal phalanx prosthesis (23) is sized and configured to be fixed to a proximal phalanx, and a proximal end of the third proximal phalanx prosthesis (23) is provided with a third turning tip (43), a third bowl-shaped gasket (53) is provided between the third receiving groove (33) and the third turning tip (43), and the third turning tip (43) is fixed rotatably in the third bowl-shaped gasket (53), and the third bowl-shaped gasket (53) is fixed rotatably in the third receiving groove (33);

wherein, the third turning tip (43) can rotate in any direction, the proximal end of the third proximal phalanx prosthesis (23) is provided with a third curved rod (73), and the third proximal phalanx prosthesis (23) is connected with the third turning tip (43) through the third curved rod (73);

the third curved rod (73) is bent toward the inner side of the finger;

the third curved rod (73) is bent at an angle of 30 to 45 degrees.

7. The bionic artificial interphalangeal joint according to claim 6, wherein:
    a wall of the third receiving groove (33) is provided with a third notch (83) in the direction close to the inner side of the finger,
    the third bowl-shaped gasket (53) is provided with a fourth notch (84) in the direction close to the inner side of the finger,
    and when the third proximal phalanx prosthesis (23) is bent to the inner side of the finger, the third curved rod (73) can be inserted into the third notch (83) and the fourth notch (84), so that the third proximal phalanx prosthesis (23) is bent toward the inner side of the finger at an angle above 90 degrees.

8. The bionic artificial interphalangeal joint according to claim 6, wherein:
    the third proximal phalanx prosthesis (23) is provided with a third bending limit stopper (63),
    when the third proximal phalanx prosthesis (23) is bent at a predetermined angle relative to the third metacarpal prosthesis (13) under an action of external force, the third bending limit stopper (63) abuts against the third metacarpal prosthesis (13), thereby restricting the third proximal phalanx prosthesis (23) from continuing to bend.

* * * * *